United States Patent [19]

Zoechbauer

[11] Patent Number: 5,059,026
[45] Date of Patent: Oct. 22, 1991

[54] INTERFEROMETRIC DEVICE HAVING A CONTROLLABLE FABRY-PEROT

[75] Inventor: Michael Zoechbauer, Oberursel, Austria

[73] Assignee: Hartmann & Braun AG, Frankfurt, Fed. Rep. of Germany

[21] Appl. No.: 551,419

[22] Filed: Jul. 12, 1990

[30] Foreign Application Priority Data

Jul. 19, 1989 [DE] Fed. Rep. of Germany ....... 3923831

[51] Int. Cl.$^5$ .............................................. G01B 9/02
[52] U.S. Cl. .................................... 356/346; 356/352
[58] Field of Search .................... 356/352, 346, 351

[56] References Cited

U.S. PATENT DOCUMENTS 4,999,013  3/1991  Zoechbauer et al. ............... 356/346

Primary Examiner—Samuel Turner
Assistant Examiner—Richard E. Kurtz, II
Attorney, Agent, or Firm—Ralf H. Siegemund

[57] ABSTRACT

An interferometric device for the detection of substances having a periodic or quasiperiodic absorption structure of their absorption spectrum includes a source of radiation, a chamber containing the material to be investigated and a downstream detector, a thermo-optically effective and temperature controlled interference filter means is interposed, its thickness determines the spacing of interference transmission lines and temperature control shifts these lines.

6 Claims, 2 Drawing Sheets

SUBSTANCE ABSORPTION

Fig. 1a

WAVE LENGTH

FILTER E TRANSMISSION

MEASURING PHASE

Fig. 1b

WAVE LENGTH

FILTER E TRANSMISSION

REFERENCE PHASE

Fig. 2

WAVE LENGTH

INTERFEROMETRIC DEVICE HAVING A CONTROLLABLE FABRY-PEROT

BACKGROUND OF THE INVENTION

The present invention relates to interferometric equipment for detecging a substance having a molecular structure such that it exhibits a periodic or quasiperiodic absorption spectrum, the equipment uses a source of radiation and a detector.

Copending application (Ser. No. 338,723, filed Apr. 14, 1989) corresponding to German application P38 12 334 describes interferometric equipment for detecting a substance with a periodic or quasiperiodic absorption spectrum using an electrically tunable interference filter. That filter is basically comprised of a plate made of an electrooptical material having its major flat sides provided with reflecting but semitransparent surface layers and boundaries. The thickness of the plate is selected to meet one of the following criteria.

The distance between the interference lines that are being produced by that particular filter equals a distance of the absorption lines within a periodic absorption spectrum of the substance to be detected; an alternative feature requires the thickness of the filter plate to be selected so that the bandwidth of an absorption line that can be separated is quite small as compared with the spacing between two absorption lines of that subject to be detected. A third alternative requires that a line as separated from the radiation will overlap an edge of the absorption band or of an absorption band of the substance to be detected.

The interferometric equipment of the kind described in the preceding paragarph can also be modified in that in lieu of a plate a cell which is filled with a double refracting liquid crystal filling is provided. Again however the windows are on the inside provided with a semitransparent reflective coating.

This particular equipment is highly useful and the principles employed have been deemed very successful, but there are certain substances where its employment seems less suitable. For example, if the presence or existence of carbon monoxide (CO) is selectively detected by using a wavelength of 4.6 micrometers, the following problems arise. For example, a lithium-niobate plate of appropriate thickness as far as the optical requirements are concerned can be selected, but electrical breakthrough may occur already at a controlled voltage as applied which is well below the voltage deemed optimum for purposes of the detection. In other words there is a discrepancy between the theoretical optimum sensitivity and a practical physical constraint for other reasons. On the other hand if a liquid crystal embodiment is used then the cell thicknesses that will be needed for obtaining resonance conditions are at values which are not adequately subject to tolerance control. Therefore these two kinds of equipment are not suitable for CO measurement. In fact similar difficulties are to be expected in all those cases in which the absorption lines have comparable spacing as compared with CO.

DESCRIPTION OF THE INVENTION

It is an object of the present invention to provide a new and improved interferometric equipment for the detection of substances and more particularly it is an object of the present invention to improve structure for the detection of substances exhibiting periodically or quasiperiodically structured absorption spectrum;

it is a specific object of the present invention to provide a new interferometric device for the detection of particular substances on the basis of their periodic or quasiperiodic absorption spectra by using an interference filter, thickness of which is determinative of the characteristic features utilized in the detection process.

It is a feature of the present invention to provide and to continue to provide an interference plate with a thickness meeting one of the three following criteria. The first is that the distance of the interference lines as produced by that plate correspond to the distance of the absorption lines of the substance to be detected;

an alternative criteria is that a particular line as separated from the radiation has a band width which is small as compared with the distance between lines in the absorption spectrum of the substance to be determined;

a third alternative is that a line of the radiation is separated such that the flank and edge of this line overlaps the edge of an absorption band of the substance under investigation;

in accordance with the preferred embodiment of the present invention the objects are attained and the features are utilized by employment of an interference filter with a thermooptically tunable filter element being comprised of a plate made of thermooptic active material having flat sides which are provided with semi-transparent reflective surface coatings. A shift of the transmission characteristics of the filter is produced by using temperature changes whereby the temperature difference is a quantitative indication for that shift.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIGS. 1a, b and 2 illustrate absorption and transmission diagrams relevant to the practice of the invention whenever a periodic or quasiperiodic line spectrum of the substance to be detected is expected;

Figure 3:
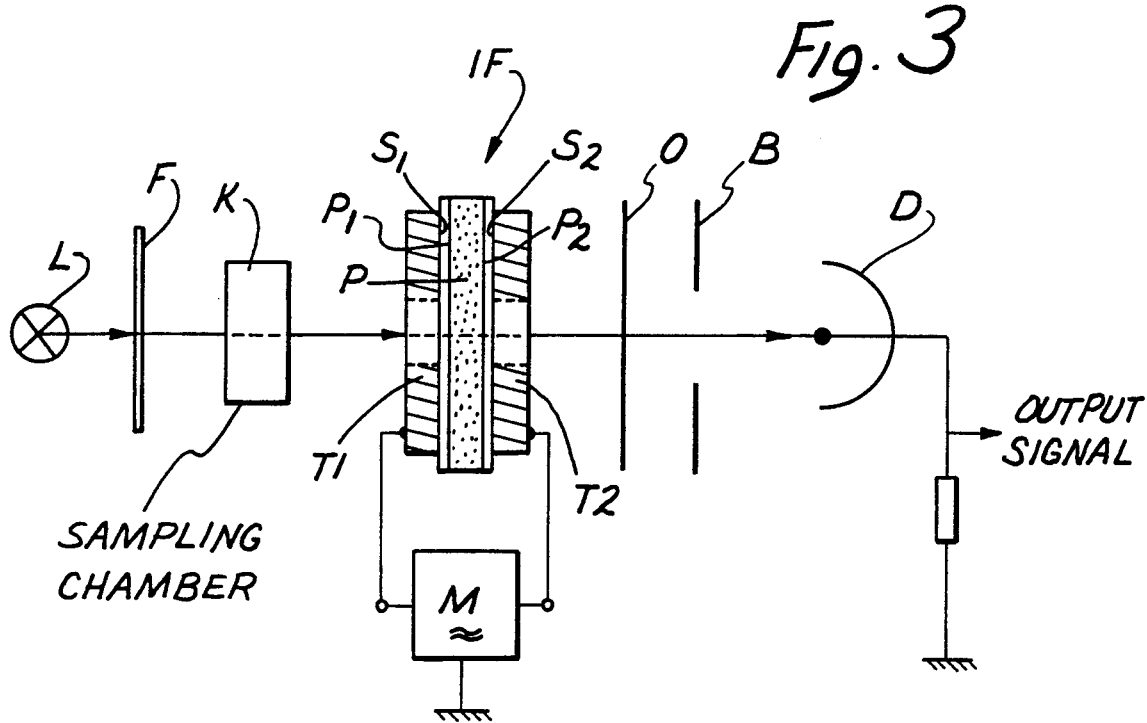
FIG. 3 is a schematic showing of a preferred embodiment of the present invention for practicing the best mode of the invention.

It can therefore be seen that the critical portion of the invention is the utilization of a thermooptically tunable filter made of thermooptically actgive plate so this is a material whose index of refraction and thickness changes with temperature (actually the product of these values) in an optically relevant manner. Of course one could say that many materials may have that particular characteristics, but preferably one uses a silicon plate whose thermooptical coefficient in that regard is quite high. In fact the thermal plate is worked such that a Fabry-Perot element results. Depending on the index of refraction of the material the particular degree of reflectioin results at the main surfaces which is determinative of the half way width of the fabry-perot element. If the half value width is small one can obtain this feature through supplemental mirroring and reflectivity of the front and rear surface.

Depending on the kind of spectrum, and the purpose and goal and aim of the measurement a high sensitivity may be required in one particular case. In other cases the selectivity is more important and in still other instances the adaptability to specific measuring task is the most important requirement. All these different cases require certain variations in the configuration but in principle design changes. For example when the sensitivity is to be very high (low concentration of the test substance) then one should provide a configuration which covers a relatively large part of the entire absorption spectrum. This is particularly of advantage if the substance has a period of quasiperiodic line spectrum. For example in the case of CO molecules the spectrum around 4.6 micrometers concerns that situation. In this case then the thickness of the thermooptical plate is selected so that the resulting interference pattern corresponds to the characteristic optical path difference of the molecules which is to be detected. That in fact means that the distance between the individual interference devices of the thermooptical fabry-perot element corresponds exactly to the distance of the periodic absorption line of the substance to be detected.

As a starting point it is therefore assumed that the interference pattern of the filter is as shown in FIG. 1b. Moreover, that interference filter can be brought into a matching, congruent relationship with the absorption spectrum of the particular material, as shown e.g. in FIG. 1a. The two FIGS. 1a, b are shown in vertical alignment and the dashed lines are representative of the fact that the transmission peaks of the filter match precisely the transmission absorption peaks of the particular substance. The device in this case is now in fact in a measuring phase according to which maximum absorption results. This situation is desired for maximum sensitivity.

In accordance with the principal feature of the invention on changing the temperature of the filter a shift in the transmission pattern obtains as is shown in FIG. 2. In particular now the shift is such that the transmissio peaks now lodge precisely in between the absorption peaks of the particular substance (e.g. CO). As stated the particular adjustment of the filter with a transmission pattern as shown in FIG. 1b means that the particular filter is adjusted to the measuring phase while on changing the temperature and obtaining a transmission pattern as shown in FIG. 2 thereby the reference phase is obtained as far as this filter is concerned.

It is immediately apparent that in the measuring phase the absorption by the filter is at its maximum as far as the particular spectral lines are concerned and in the reference phase there is no or very little or minimal absorption, at the very lease there is a significant detectable difference in between the two phases as far as absorption is concerned. By periodically modulating the temperature one alternates the filter between measuring and reference phase and that avoids the problems outlined above. The thermooptical modulation in other words permits measurement and detection of substances which by means of electrooptical modulation is not or hardly ascertainable.

The figures can also be used to explain the high selectivity as the second mode of realizing the invention. In this case the interferometer produces a single line having a bandwidth that is small as compared with the distance between two lines of the periodic or quasiperiodic absorption spectrum. The interferometer provides and separates a single narrow line; that line has a bandwidth that is small as compared with the distance between two lines within a periodic or quasiperiodic absorption spectrum of the substance. Through simple shifting the central wavelength of this particular filter line and across the absorption line of the substances one produces a useful signal whenever the measuring component is found to be within the absorption path. Since the correlation area to be covered is in this case smaller than in the first mentioned application with multiple lines and multiple absorption spectrum and interference pattern, one has to expect a larger noise level. On the other hand the advantage of this particular single line method is to be seen in the selection of the wavelength. One can shift it into a range wherein an overlap with any kind of interfering component is not present. This then provides a reduction in the noise level that is not available in the example mentioned above with reference to FIGS. 1a, b and 2.

The third possibility of applying the inventive method will be employed with advantage whenever the spectrum is not a periodic one but has a recognizable structural pattern which is described here as quasiperiodic. By selecting a particular wavelength in a range of relatively strong change in absorption as far as the component and substance is concerned a useful signal is indeed produced whenever that particular component is present. The wavelength for the desired component is selected so that absorption by the interfering components is either not existing at all or its gradient with wavelength i.e. its change with wavelength is relatively small, at least small as compared with the change in wavelength of the material to be detected.

For investigating and detecting different substances one simply changes the initial thickness of the plate; that is, so to speak, the starting point. Variations in thickness and shifting the absorption/transmission lines are then obtained by temperature control of the plate. With this we proceed to the description of FIG. 3 which is an example of equipment by means of which any of the three approaches can be realized. It is assumed that there is a source of radiation L which could be selective in certain cases but from a broad application point of view it may have broad band output as far as issuing emanating light is concerned. This is simply a matter of practicality and simplicity in the manufacture and design.

A first filter F limits the radiation output to that portion in which the measurement obtains. In other words overloading of whatever absorption if relied upon through excessive radiation is avoided at this stage, and the frequency of the light permitted to pass is limited by means of this filter F. It is however not the interference filter although there is no principle restriction as far as the employment of this filter F is concerned.

Downstream from the filter F is a sampling chamber K, flask, cuvette, or baloon of suitable design containing the substance to be investigated including the particular substance absence and presence of which is to be detected. Downstream now from this chamber K is disposed an interference filter IF being comprised of a thermoopticlly tunable plate P. The plate P has a face P1 facing the oncoming radiation and a face P2 facing away therefrom. Both of these faces are covered with a semitransparent mirror coating respectively S1 and S2 or semi-reflecting coating. The material for this particular plate should of course have a very large thermooptical coefficient, i.e. the product of its index of refraction and thickness (geometrical) should change with temperature in a significant way. By way of example, Si or zinc selenide are suitable.

The mirrors S1 and S2 of this device carry i.e. are provided respectively with peltier elements T1 and T2 which are controlled by an electronic circuit M. The effect thereof will be described shortly. Downstream form the electrothermal device is provided an objective i.e. a lens for collimating radiation to a focal point of a detector D. A diaphragm B may limit conveniently the radiation to axis near parallel beam portions, so as to eliminate spurious parasitic and stray signals. The detector D basically converts the optical signal into an electric one.

The circuit M driving the peltier elements changes the temperature and thereby shifts the transmission lines of the filter as shown for example FIGS. 1b and 2 or as needed as per the various cases, situations, instances and examples outlined above and concerning sensitivity, selectivity or shifting in the case of absence of a pronounced periodicity.

Figure 3A:
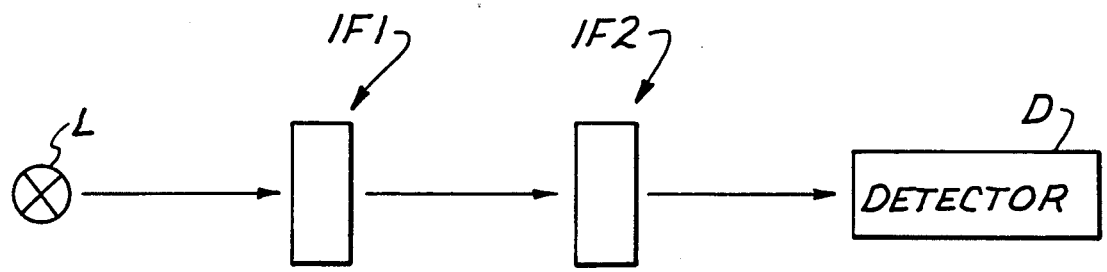
FIG. 3a shows a cascaded filter arrangement.

Turning now to FIG. 3a showing a cascaded filter arrangement. There is illustrated by accordingly and way of example an interference filter IF1 of the kind identified as IF in FIG. 3 while another similar interference filter, IF2 being of substantially the same construction, is provided in between that filter IF1 and the detector D. The two filters are attuned and attunable to different absorption characteristics of the material that is in the sampling chamber.

The invention is not limited to the embodiments described above but all changes and modifications thereof, not constituting departures from the spirit and scope of the invention, are intended to be included.

I claim:

1. Interferometric device for the detection of substances having a periodic or quasiperiodic absorption structure of their absorption spectrum including a source of radiation, a chamber containing the material to be investigated and interference filter means with a thickness that determines the spacing of interference transmission lines and a downstream detector, the improvement comprising, the filter being a thermooptically tunable filter including a plate made of thermooptical active material, and semitransparent mirror surfaces in the said radiation path; and means for variably controlling the temperature of said filter.

2. Interferometric device as in claim 1, wherein the thickness of the plate is selected so that the spacing of the interference lines as produced corresponds to the spacing of the absorption line of the substance to be detected, said temperature control shifting the interference lines from matching to nonmatching relationships as far as the transmission lines of the filter are concerned in relation to the absorption lines of said substance.

3. Interferometer as in claim 1, said interference filter in conjunction with the source of radiation providing a transmission line having a bandwidth which is small as compared with the spacing between two absorption lines of said substance, said control means shifting the transmission line of said plate between a matching position with regard to one of said absorption lines, and an in between position.

4. Interferometer as in claim 1, said plate being adjusted in thickness so that a line of the radiation as transmitted covers a steeply varying portion of the absorption vs. frequency characteristics of the substance to be detected.

5. Interferometer as in claim 1, said thermooptically active material being silicon or a silicon compound.

6. An interferometric system comprising an interferometric device as in claim 1 as well as another thermooptically active and controllable interference filter upstream from said detector.

* * * * *